(12) United States Patent
Hashimoto et al.

(10) Patent No.: US 7,949,160 B2
(45) Date of Patent: May 24, 2011

(54) IMAGING APPARATUS AND IMAGING METHOD

(75) Inventors: Hiroshi Hashimoto, Tokyo (JP); Koji Miyama, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 986 days.

(21) Appl. No.: 11/760,898

(22) Filed: Jun. 11, 2007

(65) Prior Publication Data

US 2008/0058643 A1    Mar. 6, 2008

(30) Foreign Application Priority Data

Jun. 15, 2006 (JP) .................................. 2006-165893

(51) Int. Cl.
*G06K 9/00* (2006.01)
(52) U.S. Cl. .......................... 382/128; 382/131; 382/154
(58) Field of Classification Search .................. 382/128, 382/131, 154
See application file for complete search history.

(56) References Cited

U.S. PATENT DOCUMENTS

| 5,746,208 | A | 5/1998 | Prince |
| 5,879,302 | A | 3/1999 | Hashimoto et al. |
| 6,102,858 | A | 8/2000 | Hatfield et al. |
| 6,546,068 | B1 * | 4/2003 | Shimura .......................... 378/19 |
| 6,980,622 | B2 * | 12/2005 | Nukui ................................ 378/4 |
| 7,142,633 | B2 | 11/2006 | Eberhard et al. |
| 7,167,740 | B2 | 1/2007 | Abe et al. |
| 2005/0226375 | A1 | 10/2005 | Eberhard et al. |
| 2006/0050963 | A1 | 3/2006 | Suzuki et al. |
| 2006/0067567 | A1 | 3/2006 | Hashimoto |
| 2006/0165270 | A1 | 7/2006 | Borgert et al. |

FOREIGN PATENT DOCUMENTS

| JP | 3365929 B | 6/1998 |
| JP | 10171976 | 6/1998 |
| JP | 2001-118086 | * 4/2001 |
| JP | 2002165776 | 6/2002 |
| JP | 2005160784 | 6/2005 |
| JP | 2006122643 | 5/2006 |

* cited by examiner

*Primary Examiner* — Tom Y Lu
(74) *Attorney, Agent, or Firm* — Armstrong Teasdale LLP

(57) ABSTRACT

In executing projection processing for the purpose of enhancing the efficiency of diagnosis, if a threshold is reached again after a specific value of a pixel reaches the threshold in the x direction in which tomographic planes are arrayed, the execution of the projection processing is ended, and a projected image is generated. Then, in generating that projected image by executing projection processing, tomograms are so synthesized with the projected image that the positions of the pixels projected in the x direction and the pixels of the tomograms generated in the x direction match each other in the scanned three-dimensional area of the subject, and the synthesized images are thereby generated.

19 Claims, 6 Drawing Sheets

IMAGING APPARATUS AND IMAGING METHOD

CROSS REFERENCE TO RELATED APPLICATIONS

This application claims the benefit of Japanese Patent Application No. 2006-165893 filed Jun. 15, 2006.

BACKGROUND OF THE INVENTION

The present invention relates to an imaging apparatus and an imaging method.

Imaging apparatuses such as an ultrasonic diagnosing apparatus, an X-ray CT apparatus and a magnetic resonance imaging apparatus generate tomograms regarding tomographic planes of a subject. An ultrasonic diagnosing apparatus, for instance, transmits an ultrasonic wave to a subject, generates a tomogram regarding a tomographic plane of the subject on the basis of the ultrasonic wave reflected by the subject and received, and displays the tomogram on a screen.

In an ultrasonic diagnosing apparatus, there are a number of imaging modes including a B mode, a color flow mapping (CFM) mode, and a pulse wave Doppler (PWD) mode. Since this ultrasonic wave diagnosing apparatus can generate and display an image on a real-time basis, it is extensively used in various fields of medicine including fetal examination and cardiac examination in particular.

In an imaging apparatus such as an ultrasonic diagnosing apparatus, a projected image is generated by subjecting tomograms regarding a plurality of tomographic planes in a subject, and the projected image thereby generated is displayed. For instance, it processes maximum intensity projection (MIP) is executed to project the pixels taking on the maximum value in the arrayed direction of the tomographic planes regarding which the plurality of tomograms are generated, and thereby generates an MIP image as the projected image (see Patent Document 1 for example).

[Patent Document 1] Japanese Patent No. 3365929

Incidentally, where an imaging apparatus such as the one referenced above is used, imaging may be carried out after injecting a contrast medium into the subject. For instance, when imaging is to be carried out by using an ultrasonic diagnosing apparatus, after injecting a contrast medium containing micro-bubbles into a blood vessel of the subject in which blood is flowing, the plurality of frames of tomograms are picked up as three-dimensional images. Then, this plurality of frames of tomograms are displayed as moving images consecutively in a time series. This makes it possible to observe how the contrast medium proceeds in the blood vessel, and the observation is used for diagnostic purposes.

However, in the tomogram of each frame, only the part where the contrast medium is positioned in the whole blood vessel at the time of picking up the tomogram of that frame is displayed in high contrast, and other areas are displayed only in low contrast, with the result that when the tomograms of that plurality of frames are to be consecutively displayed as moving images, sometimes it is not easy to keep track of the procession of the contrast medium in the whole blood vessel of the subject. Thus, since the shape of the whole blood in which the contrast medium proceeds is not highly contrastive, it is not easy to accurately keep track of the procession of the contrast medium in the whole blood vessel. This sometimes invites a drop in the efficiency of diagnosis.

In this way, when image diagnosis is to be carried out with an imaging apparatus, trouble of low diagnostic efficiency may occur.

SUMMARY OF THE INVENTION

Therefore, an object of the present invention is to provide an imaging apparatus and an imaging method which enable the efficiency of diagnosis to be enhanced.

In order to achieve the object stated above, an imaging apparatus according to the invention has a tomogram generating unit which successively generates a tomogram regarding each of a plurality of tomographic planes arrayed in different positions in a three-dimensional area of a subject; a projected image generating unit which generates a projected image by so executing projection processing of specific values of pixels in the tomogram generated by the tomogram generating unit for each of a plurality of tomographic planes arranged in the direction in which the tomographic planes are arrayed; and a synthesized image generating unit which generates a plurality of synthesized images by synthesizing the tomograms generated by the tomogram generating unit with a projected image generated by the projected image generating unit, wherein the projected image generating unit, upon executing the projection processing, when a threshold is reached again after a specific value of a pixel reaches the threshold in the direction in which the tomographic planes are arrayed, ends the projection processing; and the synthesized image generating unit so synthesizes each of the tomograms with the projected image that the positions of pixels of the tomograms generated by the tomogram generating unit in the direction in which the tomographic planes are arrayed and the positions of pixels projected in the direction in which the tomographic planes are arrayed when the projected image generating unit executes the projection processing match each other in the three-dimensional area.

Also in order to achieve the object stated above, an imaging method according to the invention has a tomogram generating step of successively generating a tomogram regarding each of a plurality of tomographic planes arrayed in different positions in a three-dimensional area of a subject; a projected image generating step of generating a projected image by so executing projection processing of specific values of pixels in the tomogram generated at the tomogram generating step for each of a plurality of tomographic planes arranged in the direction in which the tomographic planes are arrayed; and a synthesized image generating step of generating a plurality of synthesized images by synthesizing the tomograms generated at the tomogram generating step with a projected image generated at the projected image generating step, wherein the projection processing is ended at the projected image generating step upon executing the projection processing, when a threshold is reached again after a specific value of a pixel reaches the threshold in the direction in which the tomographic planes are arrayed; and each of the tomograms is so synthesized with the projected image at the synthesized image generating step that the positions of pixels of the tomograms generated at the tomogram generating step in the direction in which the tomographic planes are arrayed and the positions of pixels projected in the direction in which the tomographic planes are arrayed when the projection processing is executed at the projected image generating step match each other in the three-dimensional area.

According to the invention, it is possible to provide an imaging apparatus and an imaging method which enable the efficiency of diagnosis to be enhanced.

Further objects and advantages of the present invention will be apparent from the following description of the preferred embodiments of the invention as illustrated in the accompanying drawings.

DETAILED DESCRIPTION OF THE INVENTION

Apparatus

An ultrasonic wave diagnosing apparatus 1 will be described as an imaging apparatus, which is a preferred embodiment of the invention.

Figure 1:
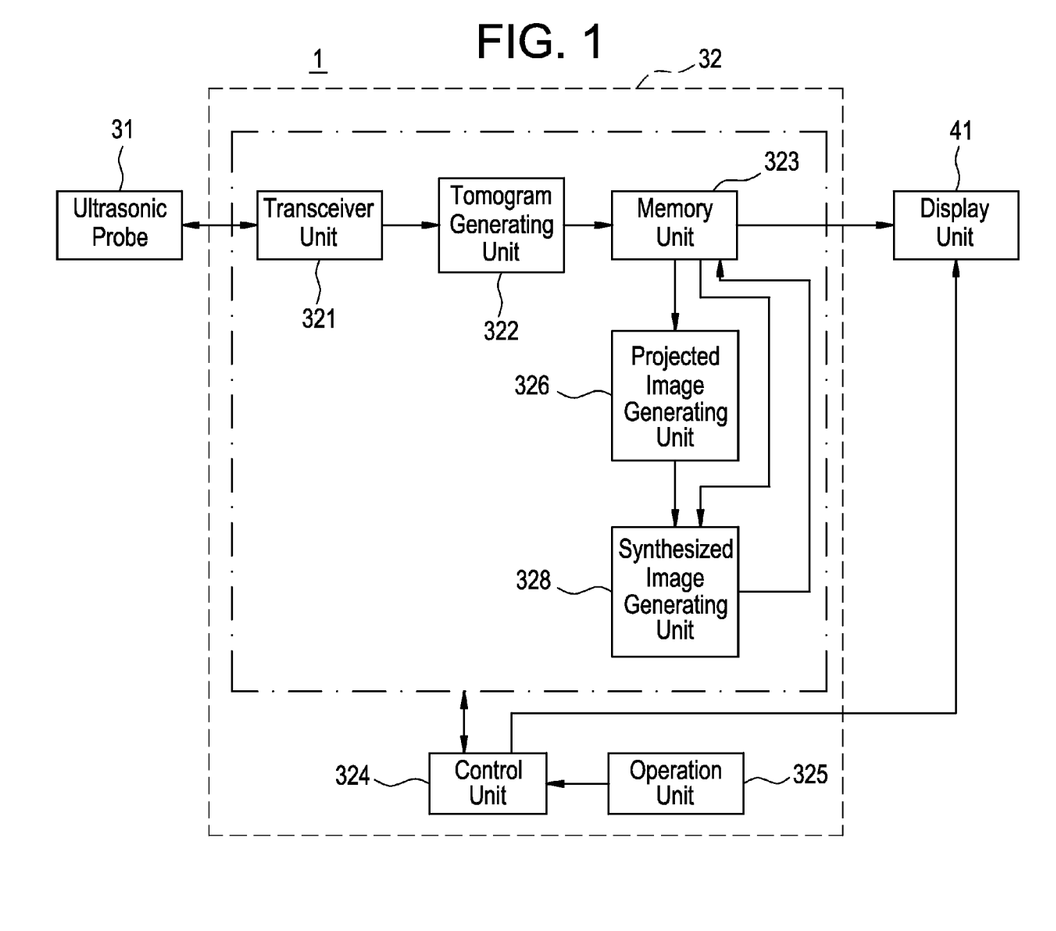
FIG. 1 is a block diagram showing the configuration of an ultrasonic diagnosing apparatus 1, which is a preferred embodiment of the present invention.

FIG. 1 is a block diagram showing the configuration of the ultrasonic diagnosing apparatus 1, which is the preferred embodiment of the invention.

As shown in FIG. 1, the ultrasonic diagnosing apparatus 1 embodying the invention has an ultrasonic probe 31, an operation console 32 and a display unit 41. These constituent units will be successively described below.

The ultrasonic probe 31 includes a plurality of ultrasonic vibrators (not shown), which are uniformly arrayed therein. In the ultrasonic probe 31, the ultrasonic vibrators, which contain a piezoelectric material such as lead zirconium titanate (PZT) ceramic, convert electrical signals into sound waves and transmit them, and convert received sound waves into electrical signals, which are outputted as echo signals. The ultrasonic probe 31 is used with its face provided with the ultrasonic vibrators kept in contact with the surface of the subject. While details will be described afterwards, the ultrasonic probe 31 so transmits ultrasonic waves from the ultrasonic vibrators into the subject as to match a drive signal from a transceiver unit 321, based on a control signal outputted from a control unit 324 in an operation console 32, and acquires echo signals as raw data by executing a scan by which ultrasonic waves reflected from the subject into which those ultrasonic wave are transmitted are received by the ultrasonic vibrators. Then it outputs those echo signals to the transceiver unit 321. In this embodiment, the ultrasonic probe 31 scans, in the subject in which the contrast medium is injected into a fluid, a three-dimensional area including the fluid in which the contrast medium flows.

The operation console 32, as shown in FIG. 1, has the transceiver unit 321, a tomogram generating unit 322, a memory unit 323, the control unit 324, an operation unit 325, a projected image generating unit 326 and a synthesized image generating unit 328. In the operation console 32, each unit includes a data processor, which processes various data.

The transceiver unit 321, which includes a transceiver circuit which causes the ultrasonic probe 31 to transmit and receive ultrasonic waves, causes ultrasonic waves to be transmitted from the ultrasonic vibrators of the ultrasonic probe 31 to the subject in accordance with a control signal from the control unit 324, and acquires an echo signal by causing ultrasonic waves reflected by the subject to be received by the ultrasonic vibrators. For instance, the transceiver unit 321 acquires the echo signal by scanning the subject by an electronic convex scanning system, and outputs the acquired echo signal to the tomogram generating unit 322. More specifically, the transceiver unit 321 acquires the echo signal by so changing over the positions of the plurality of ultrasonic vibrators in the ultrasonic probe 31 as to scan the subject by shifting an ultrasonic wave beam, subjects the echo signal to amplification, delaying, addition and other modes of processing, and outputs the processed echo signal to the tomogram generating unit 322.

The tomogram generating unit 322 generates tomograms regarding tomographic planes of the subject on the basis of the echo signal obtained by the ultrasonic probe 31. The tomogram generating unit 322 is so controlled by the control unit 324 as to match an instruction inputted to the operation unit 325, and generates tomograms such as B mode images, Doppler images and harmonic images. More specifically, the tomogram generating unit 322, which includes a logarithmic amplifier and an envelope detector, detects an envelope after logarithmically amplifying the echo signal outputted by the transceiver unit 321. Then, after computing the intensities of echoes from the reflection points on a sound ray by subjecting the data to prescribed processing, the tomogram generating unit 322 converts the intensities into luminance values to generate a tomogram matching the B mode. The tomogram generating unit 322, which also includes an orthogonal detector and a Doppler power computing device, executes MTI processing after subjecting the echo signal outputted by the transceiver unit 321 to orthogonal detection, figures out the Doppler power value by computing the in-phase component and the orthogonal component obtained by the orthogonal detection, and generates a Doppler image. The tomogram generating unit 322, connected to the memory unit 323, outputs the tomogram generated as described above to the memory unit 323. In this preferred embodiment, the tomogram generating unit 322 successively generates a tomogram regarding each of the plurality of tomographic planes arrayed in different positions in the three-dimensional area of the subject.

The memory unit 323, so configured as to include a cine-memory and an HDD, stores the image data of the tomograms generated by the tomogram generating unit 322. The memory unit 323, connected to the tomogram generating unit 322, after temporarily storing the plurality of frames of tomograms generated by the tomogram generating unit 322 into the cine-memory in accordance with an instruction from the control unit 324, outputs them to an HDD to have them stored. For instance, the memory unit 323 stores into its cine-memory tomograms of frames equivalent to two minutes, and outputs those tomograms of frames equivalent to two minute to the HDD to have them stored. Besides that, it stores into the HDD synthesized by the synthesized image generating unit 328. The cine-memory of the memory unit 323 is connected to the display unit 41, and data on the tomograms of frames stored in the cine-memory are outputted to the display unit 41. The HDD of the memory unit 323 is also connected to the display unit 41, to which data on the tomograms of frames stored in the HDD are outputted to the display unit 41 in accordance with an instruction inputted to the operation unit 325. Also, synthetic images generated by the synthesized image generating unit 328 are outputted from the HDD to the display unit 41 and displayed thereon.

The control unit 324 includes, for instance, a computer and a program which causes the computer to execute prescribed data processing, and is connected to each constituent unit. In this embodiment, the control unit 324 gives a control signal to each of the constituent units in accordance with operation signals from the operation unit 325 and controls its operation.

The operation unit 325 includes such input devices as a keyboard, a touch panel, a track ball, a foot switch and an aural input device. The operation unit 325, to which operational information is inputted by the operator, outputs control signals to the control unit 324 on the basis of the operational information.

The projected image generating unit 326 includes a computer and a program which causes the computer to execute prescribed data processing, and generates a projected image by so executing projection processing as to arrange specific values of pixels in the tomogram generated by the tomogram generating unit 322 regarding each of the plurality of tomographic planes in the direction in which those tomographic planes are arrayed. Here, the projected image generating unit 326 receives tomograms from the memory unit 323. In the execution of projection processing, when a threshold is reached again after a specific value of a pixel reaches the threshold in the direction in which the tomographic planes are arrayed, the projected image generating unit 326 ends the execution of that particular projection processing. In this embodiment, the projected image generating unit 326 projects the maximum value as its specific value, and generates a projected image from that projected maximum.

The synthesized image generating unit 328 includes a computer and a program which causes the computer to execute prescribed data processing, and generates a plurality of synthesized images by synthesizing each of the tomograms generated by the tomogram generating unit 322 with the projected image generated by the projected image generating unit 326. Here, the synthesized image generating unit 328 so synthesizes each of the tomograms with the projected image that the positions of pixels of the tomograms generated by the tomogram generating unit 322 in the direction in which the tomographic planes are arrayed and the positions of pixels projected in the direction in which the tomographic planes are arrayed when the projected image generating unit 326 executes projection processing match each other in the three-dimensional area scanned in the subject. More specifically, the synthesized image generating unit 328 so aligns the respective pixels of the tomograms and the projected image as to be in the same coordinate positions in the three-dimensional area scanned in the subject, and executes image synthesis by, for instance, adding the values of the respective pixels to generate a synthesized image. Then, the synthesized image generating unit 328 outputs the synthesized image so generated to the memory unit 323 and causes it to be stored therein.

The display unit 41 includes, for instance, an LCD device (not shown) having a flat display screen and a digital scan converter (DSC), and displays images generated by the tomogram generating unit 322 and stored by the memory unit 323. Here, the display unit 41 successively so displays the plurality of frames of tomograms stored by the memory unit 323 as to match the sequence of the time series in which the tomogram generating unit 322 generated that plurality of frames. More specifically, the display unit 41, which is connected to the memory unit 323, converts in accordance with an instruction from the control unit 324 the data of the frames of tomograms stored in the cine-memory of the memory unit 323 into display signals with the DSC, and displays them as tomograms on the display screen of the LCD device. The display unit 41, also connected to the HDD of the memory unit 323, receives in accordance with an instruction inputted by the operator to the operation unit 325 data on an image stored in the HDD, and displays that image on the screen. Besides that, in this embodiment, the display unit 41 receives a synthesized image generated by the synthesized image generating unit 328 from the memory unit 323, and displays it on the display screen. Here, the display unit 41 successively so displays each synthesized image as to match the direction in which the tomographic planes on which the tomograms are generated in the three-dimensional area of the subject.

[Operation]

The imaging method in this preferred embodiment of the invention will be described below. This embodiment is a case in which the ultrasonic diagnosing apparatus 1 described above is used for imaging.

Figure 2:
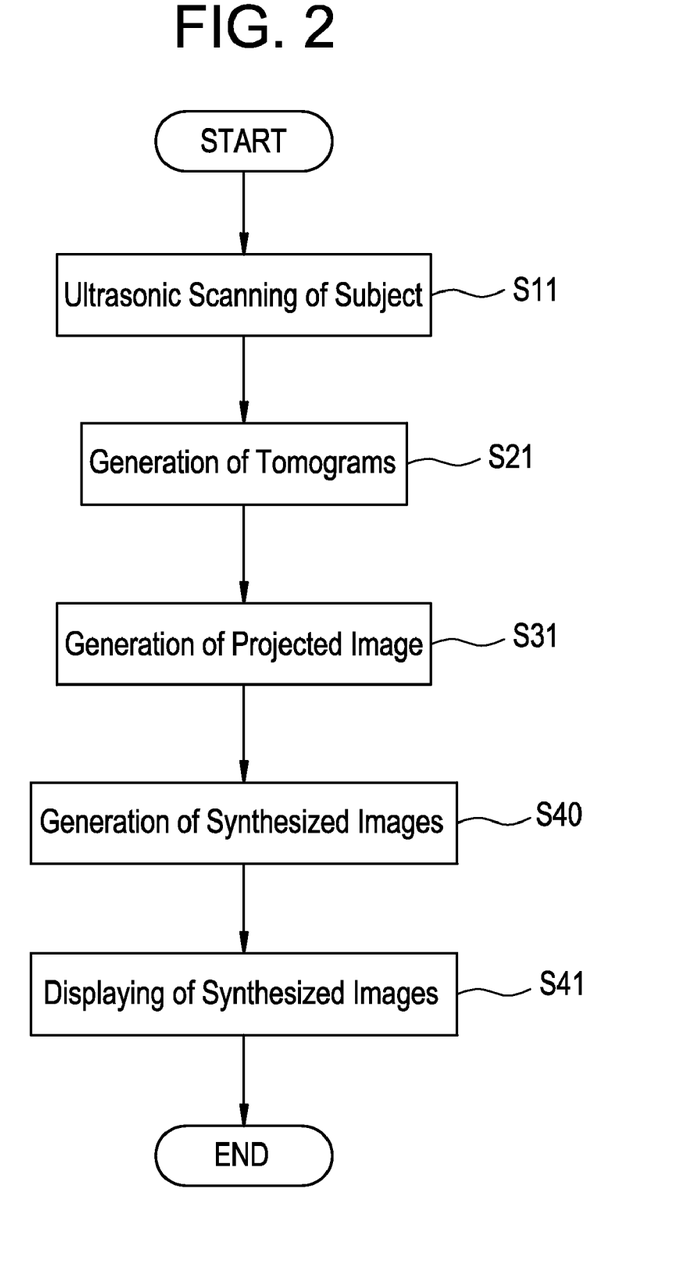
FIG. 2 is a flow chart of an imaging method according to the invention.

FIG. 2 is a flow chart of the imaging method in this embodiment of the invention.

As charted in FIG. 2, first the subject is ultrasonically scanned (S11).

In this flow, after a contrast medium is injected into a blood vessel of the subject in which blood is flowing, a three-dimensional area in that subject including the area in which the contrast medium flows is scanned.

Figure 3A:
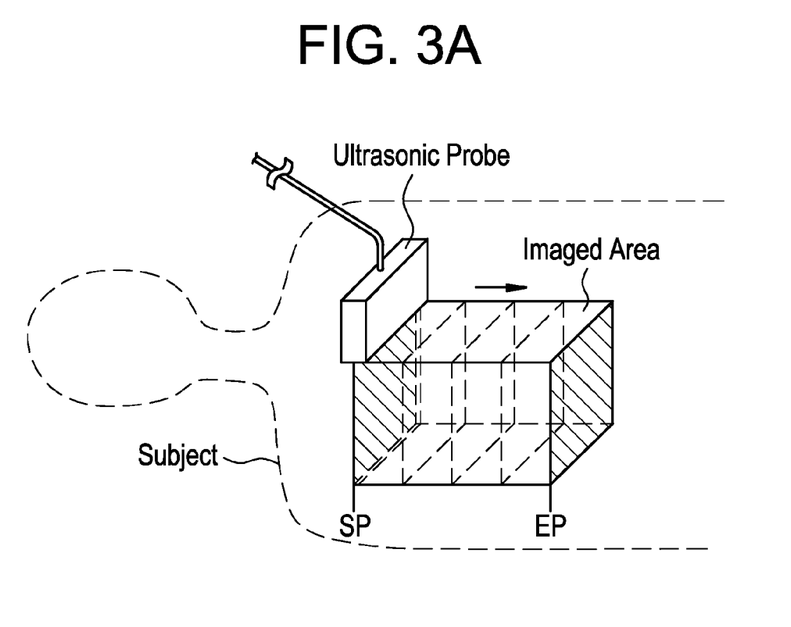
FIGS. 3a and 3b illustrate this imaging method according to the invention.
Figure 3B:
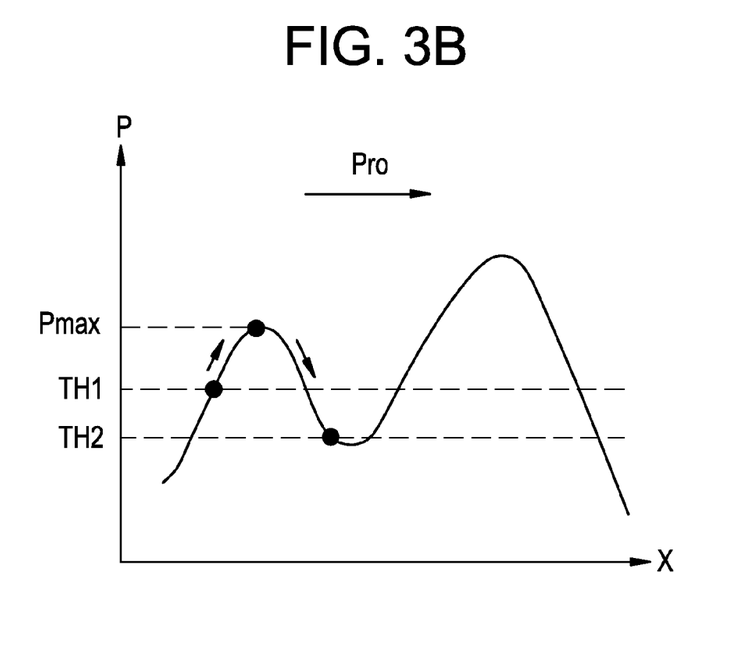

FIG. 3 illustrate the imaging method in this embodiment of the invention. In FIG. 3, FIG. 3(a) shows how the three-dimensional area in the subject is scanned. FIG. 3(b) shows the transition of a pixel value P in the plurality of generated tomograms, wherein the vertical axis represents the pixel value P and the horizontal axis, the imaging position x. Further in FIG. 3(b), the projecting direction V1 of projection processing to be described afterwards is indicated by arrows.

In this embodiment, the operator holds by hand the ultrasonic probe 31, and brings the ultrasonic probe into contact with the scan start position SP in the three-dimensional area of the subject as shown in FIG. 3(a). After that, as the operator manually moves the ultrasonic probe to the scan end position EP while keeping it in contact, the three-dimensional area is scanned. In this scanning, ultrasonic waves reflected by the three-dimensional area of the subject are received by the ultrasonic probe 31 to generate echo signals. In this embodiment, as shown in FIG. 3(b), a plurality of tomographic planes arrayed in the x direction, which is the same as the projection direction Pro, in that three-dimensional area are successively scanned in the x direction, and the echo signals obtained by this scanning are outputted by the transceiver unit 321 to the tomogram generating unit 322.

Next, a tomogram is generated as shown in FIG. 2 (S21).

Here, the tomogram generating unit 322 subjects echo signals from the transceiver unit 321 to data processing in accordance with an instruction from the control unit 324, and thereby successively generates tomograms regarding tomographic planes of the subject. In this embodiment, as shown in FIG. 3, a tomogram is successively generated regarding each of the plurality of tomographic planes arrayed in the x direction and in different positions in the three-dimensional area where the scanning is performed.

Figure 4:
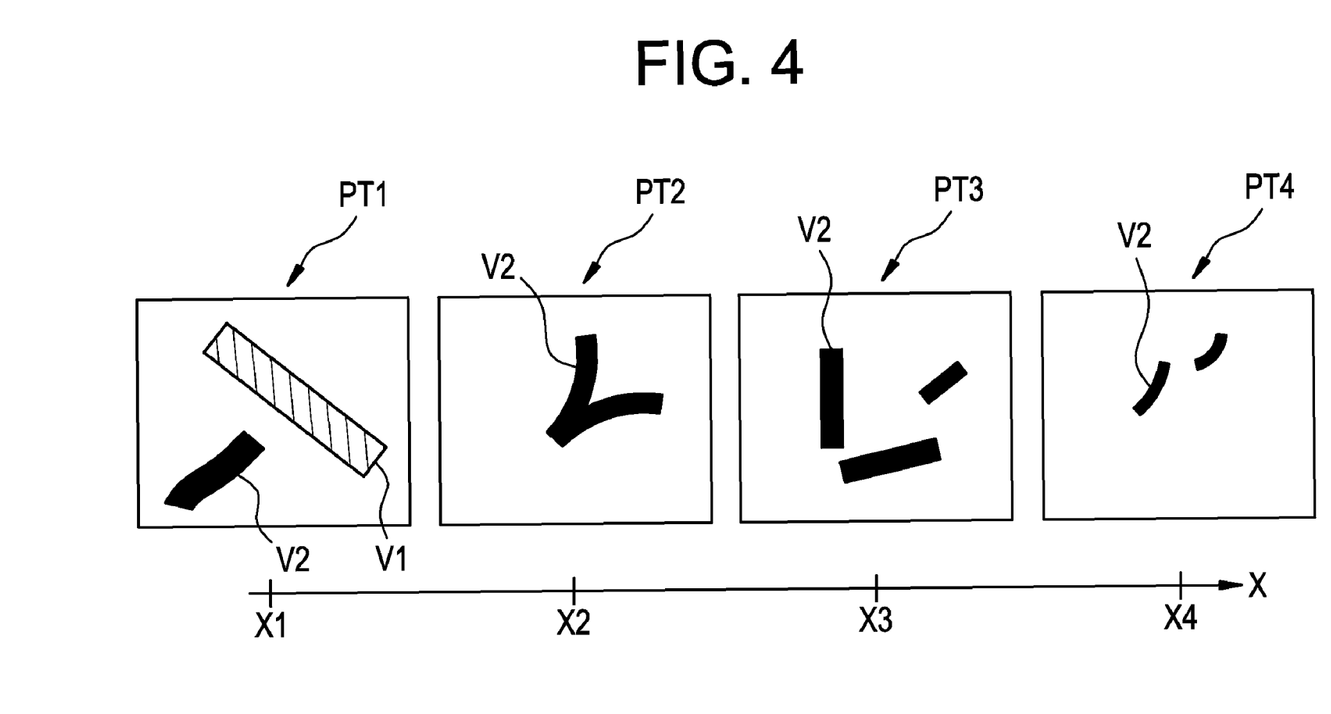
FIG. 4 shows parts of a tomogram generated in this preferred embodiment of the invention.

FIG. 4 shows parts of a tomogram generated in this embodiment of the invention. In FIG. 4, each image is reverse-displayed for the convenience of representation.

In this embodiment, as shown in FIG. 4, a plurality of tomograms PT1, PT2, PT3 and PT4 are successively generated regarding each of a plurality of tomographic plane arrayed in the x direction. Thus, a first tomogram PT1 is generated in a first position X1, a second tomogram PT2 in a second position X2, a third tomogram PT3 in a third position X3 and a fourth tomogram PT4 in a fourth position X4, all in the x direction. Here, the contrast medium is moved by the flow of blood in a blood vessel V2, and the parts to which the contrast medium has been moved are displayed in high contrast as shown in FIG. 4.

This plurality of generated tomograms are successively outputted by the tomogram generating unit 322 and caused to be outputted to the memory unit 23.

Next, as shown in FIG. 2, generation of a projected image is executed (S31).

Here, the projected image generating unit 326 generates a projected image by so executing projection processing as to project specific values of pixels in tomograms generated by the tomogram generating unit 322 regarding a plurality of tomographic planes in the direction in which their tomographic planes are arrayed. In executing this projection processing, after the specific values of pixels have reached their threshold in the direction in which their tomographic planes are arrayed, if the threshold is reached again, the execution of the projection processing will be ended. Here, the projected image generating unit 326 projects the maximum as that specific value, and generates a projected image according to that projected maximum. Thus, the projected image generating unit 326 subjects the plurality of tomograms to MIP processing.

In this embodiment, as shown in FIG. 3(b), after the pixel value P reaches a first threshold TH1 in the plurality of tomograms arrayed in the x direction, the pixel value which proves to be the maximum Pmax is projected in its projecting direction Pro, which is along the x direction. After that, if that pixel value reaches a second threshold TH2, which is smaller than that first threshold TH1, the execution of the projection processing will be ended. This processing is applied to every pixel in the tomographic plane to generate a projected image.

Figure 5:
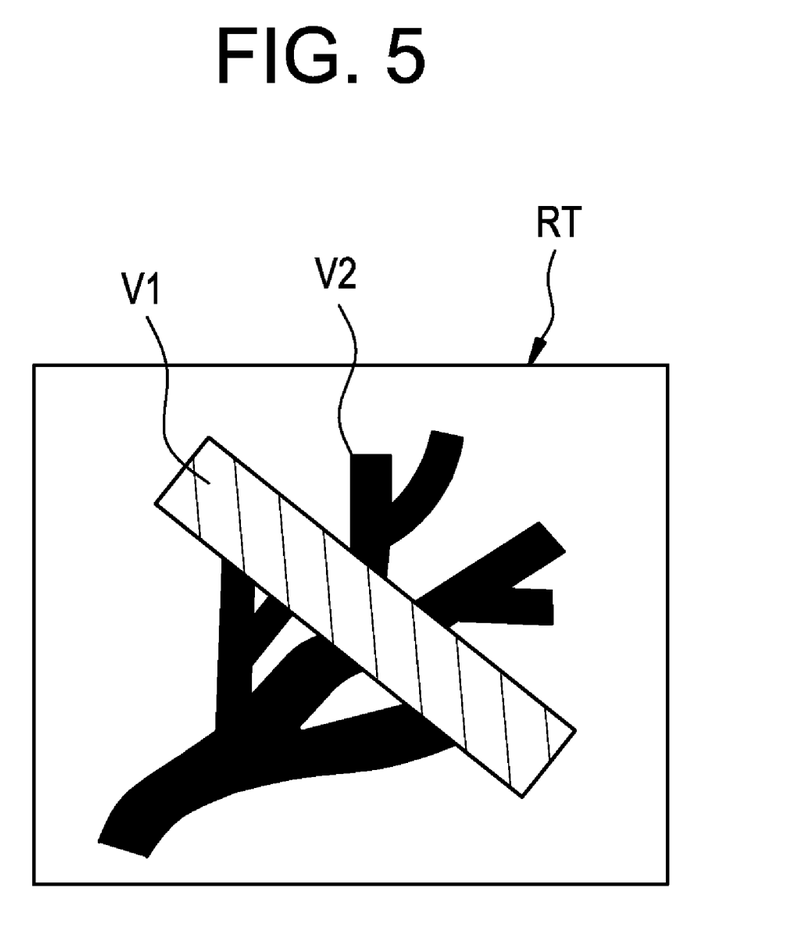
FIG. 5 shows a projected image generated in this preferred embodiment of the invention.

FIG. 5 shows a projected image generated in this embodiment of the invention.

As shown in FIG. 5, in a projected image RT, even if the value of pixels in a blood vessel V1 positioned toward the projection start point (nearer the viewer in the drawing) is lower than the value of pixels in a blood vessel V2 positioned toward the projection end point (farther from the viewer in the drawing), the value of pixels in the blood vessel V1 positioned toward the projection start point is represented. In other words, the blood vessel V1 positioned toward the projection start point is given priority and represented nearer the viewer, the blood vessel V2 positioned behind it is hidden by the blood vessel V1 shown nearer the viewer.

In this way, the projected image generating unit 326 generates a projected image, outputs it to the memory unit 323 to have it stored.

Next, a synthesized image is generated as shown in FIG. 2 (S40).

Here, the synthesized image generating unit 328 synthesizes the tomograms generated by the tomogram generating unit 322 and the projected image generated by the projected image generating unit 326 to generate a plurality of synthesized images. More specifically, the tomograms are so synthesized with the projected image that the positions of pixels in the tomograms generated in the direction in which their tomographic planes are arrayed and the positions of pixels projected in the direction in which their tomographic planes are arrayed when the projection is processed match each other in the three-dimensional area scanned in the subject.

In this embodiment, the pixels of the tomograms and the projected image are so aligned as to take on the same three-dimensional coordinate positions in the three-dimensional area scanned in the subject. After that the values of their respective pixels are synthesized to generate a synthesized image.

Thus, by synthesizing a tomogram PTi with a projected image RT as expressed in Equation (1) below, a synthesized image ATi is generated, where i is the frame number representing the position in the x direction and a and b, weighting coefficients.

$$ATi = a \cdot RT + b \cdot PTi \tag{1}$$

Figure 6:
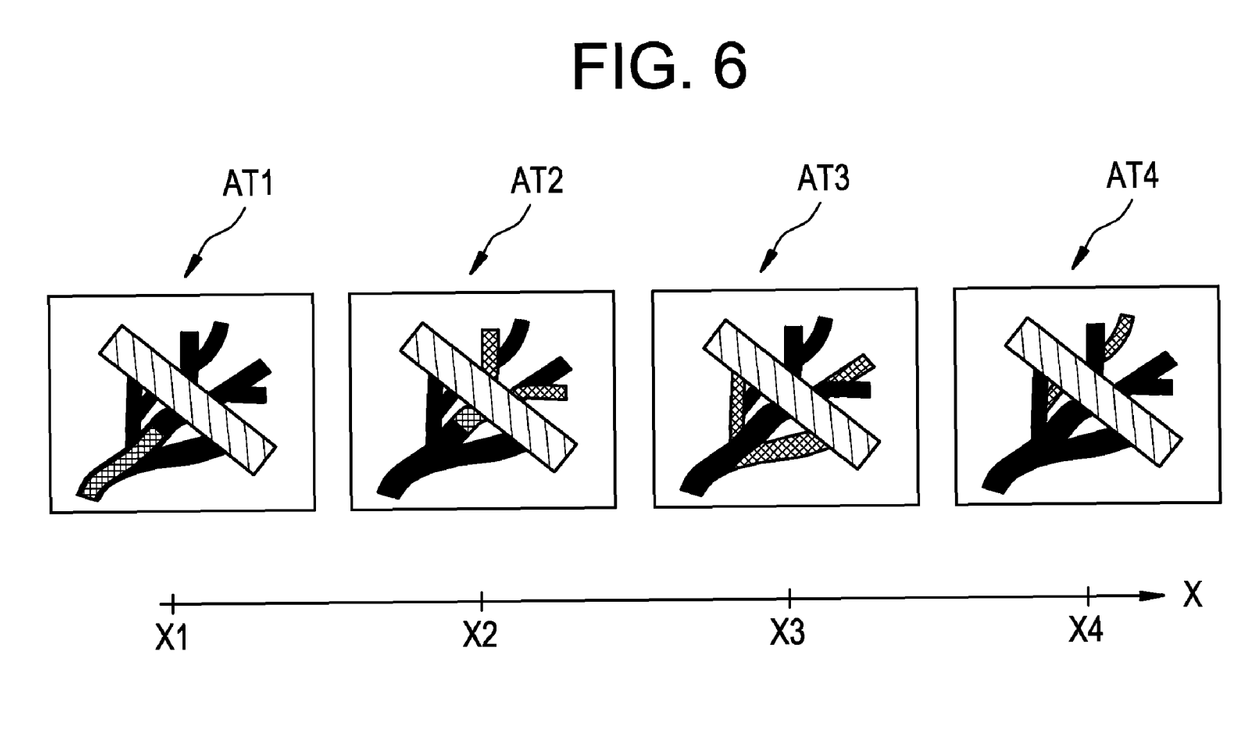
FIG. 6 shows synthesized images generated in this preferred embodiment of the invention.

FIG. 6 shows synthesized images generated in this embodiment of the invention.

In this embodiment of the invention, as shown in FIG. 6, a plurality of synthesized images AT1, AT2, AT3 and AT4 are so generated successively as to match the plurality of tomographic planes arrayed in the x direction.

More specifically, the first tomogram PT1 so generated as to match the first position X1 in the x direction as shown in FIG. 4 above and the projected image RT generated as shown in FIG. 5 are synthesized to generate the first synthesized image AT1 as shown in FIG. 6. Here, the pixels of the first tomogram PT1 and of the projected image RT are so aligned with each other as to be identical with the coordinate positions generated, when the three-dimensional area of the subject is scanned, at the three-dimensional coordinates of that three-dimensional area. Thus, the pixels of the first tomogram PT1 and of the projected image RT are so aligned with each other as to match positional information on not only the two-dimensional coordinate positions on the display screen but also the coordinate positions in the depth-wise direction of the display screen, and the pixels of both are synthesized. After that, the values of the pixels of both are added, and the first synthesized image AT1 is so generated as to be displayed in a luminance according to the added value. Similarly to the foregoing, the second tomogram PT2 generated in the second position X2 in the x direction is synthesized with the projected image RT to generate the second synthesized image AT2. Here, the blood vessel V1 positioned toward the projection start point is given priority and represented nearer the viewer, and the part matching the contrast medium flowing in the blood vessel V2 positioned behind is so displayed as to be hidden by the blood vessel V1 before that. Then, the third tomogram PT3 generated in the third position X3 in the x direction is synthesized with the projected image RT to generate the third synthesized image AT3, and the fourth tomogram PT4 generated in the fourth position X4 in the x direction is synthesized with the projected image RT to generate the fourth synthesized image AT4. After that, each of the synthesized images AT1, AT2, AT3 and AT4 so generated is outputted by the synthesized image generating unit 328 to the memory unit 323 to have it stored there.

Next, the synthesized image is displayed as shown in FIG. 2 (S41).

Here, the synthesized images generated by the synthesized image generating unit 328 are received by the display unit 41 from the memory unit 323 and displayed on the display screen. In this embodiment, the display unit 41 so displays successively the synthesized images as to match the direction in which the tomographic planes on which the tomograms are generated in the three-dimensional area of the subject are arrayed. Thus, as shown in FIG. 4, the first synthesized image AT1, the second synthesized image AT2, the third synthesized image AT3 and the fourth synthesized image AT4 are consecutively displayed in that sequence.

As described above, in executing the projection processing by this embodiment of the invention, after the specific values of pixels have reached their threshold in the x direction in which their tomographic planes are arrayed, if the threshold is reached again, the execution of the projection processing will be ended, and the projected image RT is generated. Then, in generating that projected image RT, the tomograms PT1, PT2, PT3 and PT4 are so synthesized with the projected image RP that the positions of the pixels projected in the x direction and the pixels of the tomograms PT1, PT2, PT3 and PT4 generated in the x direction match each other in the scanned three-dimensional area of the subject, and the synthesized images AT1, AT2, AT3 and AT4 are thereby generated. The synthesized images AT1, AT2, AT3 and AT4 are so displayed successively as to match the direction in which the tomographic planes on which the tomograms PT1, PT2, PT3 and PT4 are generated are arrayed in the subject. For this reason, in this embodiment, the position of the contrast medium flowing in the blood vessel is displayed with emphasis, the blood vessel V1 positioned toward the projection start point is given priority and represented nearer the viewer, and the contrast medium flowing in the blood vessel V2 behind it is so displayed as to be hidden by the blood vessel V1 positioned before it. As the position in the depth-wise direction of the display screen is taken into account and emphasized, even when another blood vessel V1 is present in the display screen before the blood vessel V2 in which the contrast medium has moved, the flow of the contrast medium in the blood vessel V2 behind, instead of the blood vessel V1 before, can be displayed emphatically. Therefore, the position to which the contrast medium has proceeded in the whole blood vessel structure can be accurately diagnosed with ease, the efficiency of diagnosis can be enhanced.

Incidentally, in carrying out the present invention, the above-described embodiment is not the only possibility, but a variety of modifications are conceivable.

For instance, though the foregoing embodiment was described with reference to tomograms generated by an ultrasonic diagnosing apparatus, the invention is not limited to this. For instance, the tomogram generating unit may as well generate tomograms on the basis of projected data obtained by detecting radiant rays irradiating and transmitted by a subject. The tomogram generating unit may also generate tomograms on the basis of magnetic resonance data obtained by an MRI apparatus from a subject in a magnetostatic field.

Further, though the foregoing embodiment was described with reference to a case in which the first threshold is greater than the second threshold when the maximum is to be projected as the specific value, this is not the only possibility. For instance, the invention may as well be applied where the first threshold is equal to the second threshold or the first threshold is smaller than the second threshold. Also, the minimum may be projected as the specific value.

Further, when such projection processing as the foregoing is to be executed, the projected image may as well be generated by subjecting the specific value of pixels in a plurality of frames of tomograms to projection processing from the depth of the display screen toward the viewer's side.

Many widely different embodiments of the invention may be configured without departing from the spirit and the scope of the present invention. It should be understood that the present invention is not limited to the specific embodiments described in the specification, except as defined in the appended claims.

The invention claimed is:

1. An imaging apparatus comprising:
   a tomogram generating unit which successively generates a tomogram regarding each of a plurality of tomographic planes arrayed in different positions in a three-dimensional area of a subject;
   a projected image generating unit which generates a projected image by executing projection processing of a specific value of pixels in the tomogram generated by said tomogram generating unit for each of a plurality of tomographic planes arranged in the direction in which said tomographic planes are arrayed; and
   a synthesized image generating unit which generates a plurality of synthesized images by synthesizing said tomograms generated by said tomogram generating unit with a projected image generated by said projected image generating unit, wherein:
   said projected image generating unit is configured to end projection processing when the specific value of a pixel reaches a second threshold after the specific value of the pixel reaches a first threshold in the direction in which said tomographic planes are arrayed; and
   said synthesized image generating unit so synthesizes each of the tomograms with the projected image that the positions of pixels of said tomograms generated by said tomogram generating unit in the direction in which said tomographic planes are arrayed and the positions of pixels projected in the direction in which said tomographic planes are arrayed when said projected image generating unit executes said projection processing match each other in said three-dimensional area.

2. The imaging apparatus according to claim 1, further comprising:
   a display unit which displays said synthesized images generated by said synthesized image generating unit, wherein:
   said display unit so displays successively said synthesized images as to match the direction in which said tomographic planes on which said tomograms are generated in the three-dimensional area of said subject are arrayed.

3. The imaging apparatus according to claim 1, wherein:
   said projected image generating unit projects the maximum as said specific value and generates said projected image according to said projected maximum.

4. The imaging apparatus according to claim 1, wherein:
   said projected image generating unit projects the minimum as said specific value and generates said projected image according to said projected minimum.

5. The imaging apparatus according to claim 1, further comprising:
   a scanning unit which obtains raw data by transmitting an ultrasonic wave to said three-dimensional area and executes a scan to receive the ultrasonic wave reflected by said subject, wherein:
   said tomogram generating unit generates said tomograms on the basis of said raw data.

6. The imaging apparatus according to claim 1, further comprising:
   a scanning unit which obtains raw data by irradiating said three-dimensional area with radiant rays and executes a scan to detect said radiant rays transmitted by said subject, wherein:
   said tomogram generating unit generates said tomograms on the basis of said raw data.

7. The imaging apparatus according to claim 1, further comprising:
   a scanning unit which obtains by irradiating said three-dimensional area with an electromagnetic wave and executes a scan to obtain raw data by detecting a magnetic resonance signal generated in said subject, wherein:
   said tomogram generating unit generates said tomograms on the basis of said raw data.

8. The imaging apparatus according to claim 5, wherein:
said scanning unit executes said scan on an area into which a contrast medium has been injected into a fluid as said three-dimensional area.

9. An imaging method comprising:
a tomogram generating step of successively generating a tomogram regarding each of a plurality of tomographic planes arrayed in different positions in a three-dimensional area of a subject;
a projected image generating step of generating a projected image by executing projection processing of a specific value of pixels in the tomogram generated at said tomogram generating step for each of a plurality of tomographic planes arranged in the direction in which said tomographic planes are arrayed; and
a synthesized image generating step of generating a plurality of synthesized images by synthesizing said tomograms generated at said tomogram generating step with a projected image generated at said projected image generating step, wherein:
the projection processing is ended when the specific value of a pixel reaches a second threshold after the specific value of the pixel reaches a first threshold in the direction in which said tomographic planes are arrayed; and
each of the tomograms is so synthesized with the projected image at said synthesized image generating step that the positions of pixels of said tomograms generated at said tomogram generating step in the direction in which said tomographic planes are arrayed and the positions of pixels projected in the direction in which said tomographic planes are arrayed when said projection processing is executed at said projected image generating step match each other in said three-dimensional area.

10. The imaging method according to claim 9, further comprising:
a displaying step of displaying said synthesized images generated at said synthesized image generating step, wherein:
said synthesized images are so displayed successively at said displaying step as to match the direction in which said tomographic planes where said tomograms are generated in the three-dimensional area of said subject are arrayed.

11. The imaging method according to claim 9, wherein:
the maximum is projected as said specific value and said projected image is generated according to said projected maximum at said projected image generating step.

12. The imaging method according to claim 9, wherein:
the minimum is projected as said specific value and said projected image is generated according to said projected minimum at said projected image generating step.

13. The imaging method according to claim 9, wherein:
said tomograms are generated on the basis of raw data obtained by transmitting an ultrasonic wave to said three-dimensional area and executing a scan to receive the ultrasonic wave reflected in said three-dimensional area at said tomogram generating step.

14. The imaging method according to claim 9, wherein:
said tomograms are generated on the basis of raw data obtained by irradiating said three-dimensional area with radiant rays and executing a scan to detect said radiant rays transmitted through said three-dimensional area at said tomogram generating step.

15. The imaging method according to claim 9, wherein:
said tomograms are generated on the basis of raw data obtained by irradiating said three-dimensional area with an electromagnetic wave and executing a scan to detect a magnetic resonance signal generated in said three-dimensional area at said tomogram generating step.

16. The imaging step according to claim 13, wherein:
said scan is executed on an area into which a contrast medium has been injected into a fluid as said three-dimensional area and said tomograms are generated on the basis of raw data obtained by the execution of said scan at said tomogram generating step.

17. A method of imaging a patient using an ultrasonic imaging system, said method comprising:
injecting a contrast medium into a subject being scanned;
generating a plurality of tomograms, wherein each tomogram is generated in different position within a three-dimensional area of the subject and such that a plurality of pixels in the tomograms are arranged in a direction in which their tomographic planes are arrayed;
processing the plurality of tomograms using a maximum intensity projection algorithm to generate a projection image;
processing the plurality of tomograms until a specific value of a pixel of the plurality of pixels reaches a second threshold after the specific value of the pixel reaches a first threshold in the direction in which the tomographic planes are arrayed; and
synthesizing the plurality of tomograms and the projection image to generate a plurality of synthesized images such that positions of the plurality of pixels in the tomograms generated in the direction in which their tomographic planes are arrayed and the positions of pixels projected in the direction in which their tomographic planes are arrayed when the projection image is processed match each other in the three-dimensional area scanned in the subject.

18. A method in accordance with claim 17 further comprising displaying the synthesized images successively to match the direction in which the tomographic images are generated in the three-dimensional area.

19. A method in accordance with claim 18 further comprising generating the plurality of tomograms using raw data obtained by irradiating the three-dimensional area with radiant rays and executing a scan to detect the radiant rays transmitted through the three-dimensional area.

* * * * *